Figure 1:
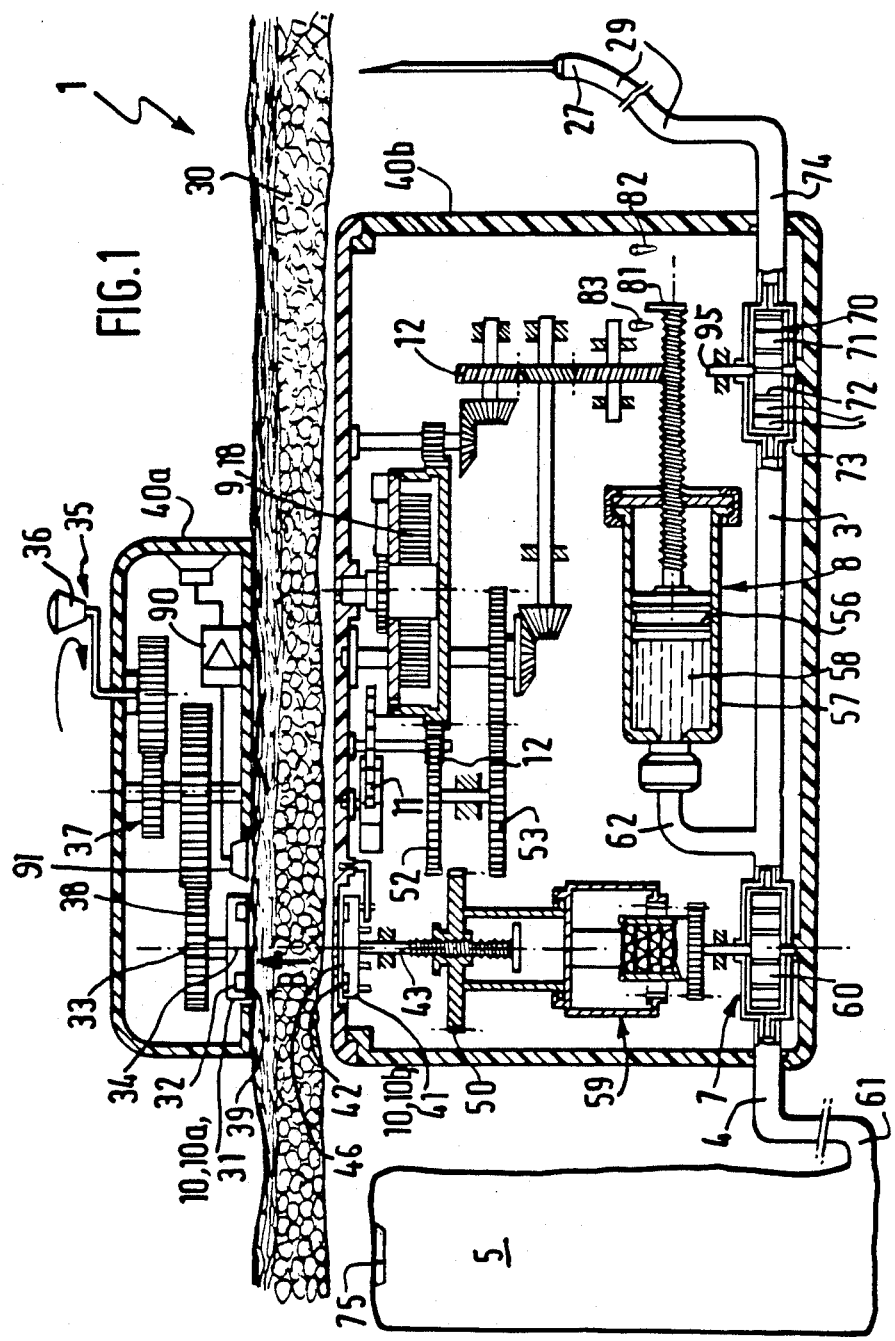

United States Patent [19]

Buffet

[11] Patent Number: 4,747,832
[45] Date of Patent: May 31, 1988

[54] DEVICE FOR THE INJECTION OF FLUID, SUITABLE FOR IMPLANTATION

[76] Inventor: Jacques Buffet, 28 Avenue Thiers, 93340 LeRaincy, France

[21] Appl. No.: 864,173

[22] Filed: May 16, 1986

Related U.S. Application Data

[63] Continuation-in-part of Ser. No. 641,444, Aug. 16, 1984, abandoned.

[30] Foreign Application Priority Data

Sep. 2, 1983 [FR] France .................... 83 14080

[51] Int. Cl.$^4$ .................................. A61M 5/20
[52] U.S. Cl. ........................ 604/135; 604/152; 604/891.1; 128/DIG. 12
[58] Field of Search ........... 604/67, 131, 134, 135, 604/151, 152, 154, 155, 891; 128/1.3–1.5, DIG. 12

[56] References Cited

U.S. PATENT DOCUMENTS

| | | | |
|---|---|---|---|
| 3,527,220 | 9/1970 | Summers | 128/1.5 |
| 3,749,098 | 7/1973 | DeBennetot | 128/346 |
| 3,817,237 | 6/1974 | Bolduc | 128/1 R |
| 4,265,241 | 5/1981 | Portner et al. | 604/891 |
| 4,300,554 | 11/1981 | Hessberg et al. | 604/135 |
| 4,411,651 | 10/1983 | Schulman | 604/891 |
| 4,443,218 | 5/1984 | DeCant, Jr. et al. | 128/DIG. 12 |
| 4,457,752 | 7/1984 | Vadasz | 604/135 |

FOREIGN PATENT DOCUMENTS

| | | | |
|---|---|---|---|
| 8100209 | 2/1981 | PCT Int'l Appl. | 604/891 |
| 2107988 | 5/1983 | United Kingdom | 604/135 |

*Primary Examiner*—C. Fred Rosenbaum
*Assistant Examiner*—Ralph Lewis
*Attorney, Agent, or Firm*—Fred A. Keire

[57] ABSTRACT

Disclosed is an implantable device for the injection of fluid into a patient's body. The device includes a non-invasive external part which magnetically cooperates with the implanted portion through a magnetic field. The device is entirely mechanical and is capable of delivering both a continuous dose of fluid as well as instantaneous dose of fluid. The mechanism comprises a fluid reservoir, a catheter, an elastic means, a regulating means, a magnetic drive means, a gear transmission means and a flow adjustment means.

15 Claims, 4 Drawing Sheets

DEVICE FOR THE INJECTION OF FLUID, SUITABLE FOR IMPLANTATION

This is a continuation-in-part of application Ser. No. 06/641,444 filed Aug. 16, 1984, now abandoned.

The present invention concerns an apparatus for fluids which are to be injected, and which can be implanted in the human body or in the body of an animal.

It is known that for the treatment of various diseases it is necessary to administer drugs continuously or intermittently, repeated over the course of the day.

Thus it is more and more common to inject fluids by means of an intramuscular, intravascular or intraperitoneal catheter. These fluids are, for instance, solutions of insulin for the treatment of diabetes, anticoagulants for persons having valve prostheses, neuroleptics, antirhythmic medicaments, anticarcinogens and medicaments for the restoring of female fertility.

The doses injected may be intermittent or continuous. In the latter case, the rate of flow must be preadjusted.

Various types of devices are at present used.

The oldest devices are external pumps, carried on a shoulder strap and connected to a catheter which passes through the skin. They are controlled by an electric circuit fed by a storage battery or dry cell. However, such devices have the drawback that the fluid may be contaminated by germs coming from the outside. Furthermore, the temperature of the fluid is not the same as the temperature of the patient's body, since the pump and the fluid reservoir are on the outside. Finally, the outside device constitutes a handicap for the patient, who cannot carry out all the desired activities such as bathing, showering, etc.

Therefore, more recently, implantable pumps have been designed which can be refilled from the outside by means of a syringe.

These pumps are either mechanical or electrical.

The mechanical pumps of the prior art, such as described in French Pat. No. 76/02 736, consist of a box which is separated into two chambers by an impermeable flexible barrier. Between the box and the barrier, there is continuously present a fluid which is in liquid/vapor equilibrium. The volume within the barrier constitutes the reservoir of fluid to be injected. Thus the vapor pressure of the fluid in phase equilibrium exerts a constant pressure on the volume of fluid to be injected, and the latter is expelled at a constant rate of flow through an outlet capillary. When the injection fluid reservoir is empty, the fluid is injected by means of a syringe, which results in the expansion of the fluid reservoir and causes the condensation of the vapor of the fluid in phase equilibrium, and the injection cycle can start again.

The fluid in phase equilibrium is a gas which liquifies near body temperature (37° C.) and consists, for instance, of butane.

Such pumps have given good results but nevertheless their main drawback is that they deliver the treatment fluid at a rate which is not adjustable and substantially constant.

Therefore, they cannot be used for the full treatment of most ailments.

Electric pumps, in general, have an electric feed such as a dry cell, an electronic circuit which makes it possible to regulate the rate of flow of the fluid to be injected with time, a reservoir containing fluid to be injected, and a pump.

These electric pumps have the drawback of comprising, in addition to the reservoir of the pumping member, an electronic circuit and a source of energy of long life. These pumps are expensive and bulky.

The invention is directed at overcoming these drawbacks.

One object of the invention therefore is to provide a device for the injection of fluids which makes it possible to obtain a rate of flow of the fluid which is variable with time. Another object of the invention is to provide a device which comprises both mechanical elements and electronic elements, only the mechanical elements being implanted since they are inexpensive, while the electronic elements, since they are expensive, are on the outside and therefore can be recovered since they are not implanted.

For this purpose, the invention concerns a device for the injection of fluids which is adapted to be implanted and which comprises in combination:

a fluid reservoir, automatic mechanical means for delivering a continuous dose of fluid into an outlet conduit, mechanical means for regulating the rate of flow of the continuous dose of fluid delivered automatically into the outlet conduit, manual mechanical means for delivering an instantaneous dose of fluid into the outlet conduit, and mechanical means for monitoring the instantaneous dose delivered.

According to the invention, the device comprises an implantable internal part and an external part. The device of the invention is characterized, in combination, by the fact that the implantable internal part comprises:

a fluid reservoir, mechanical means for pumping fluid through a conduit from a reservoir into an outlet conduit to which a catheter is connected, elastic mechanical means and mechanical means for regulating the relaxation of the elastic mechanical means, an internal part of the magnetic drive means, mechanical switching means comprising, in particular, a flow controller, and a mechanical gear transmission means between the different mechanical switching, pumping, elastic, magnetic, and regulating means, and by the fact that the external portion comprises an external part of the magnetic drive means which cooperates with the internal part of the magnetic means via a magnetic field B which passes through the skin of the patient. The device according to the invention is also characterized by the fact that the external part of the magnetic drive means enables the patient manually to drive the internal device which has been implanted through the skin in order to tension the elastic mechanical means; and/or to trigger the placing in operation of the fluid pumping means which are activated by the relaxation of the elastic mechanical means which is regulated by the regulating means, thus producing automatic mechanical means for the delivery of a continuous flow of fluid into the outlet conduit; and/or to regulate the flow of the continuous dose automatically delivered into the outlet conduit by acting on the mechanical switching means; and/or to manually deliver an instantaneous dose of fluid into the outlet conduit. The magnetic drive means are preferably formed of an external disk which cooperates magnetically with an implanted internal disk so that the manual placing in rotation of the external disk by the user results in placing the internal disk in rotation substantially at the same speed and in the same direction, the rotation in one direction $S_1$ of these disks bringing about the placing under tension of the mechanical elastic means, the opening of the switching means on the conduit between the reservoir and the pumping means, and the filling of the pumping means with fluid coming from the reservoir; the rotation in the other direction $S_2$ of the disks brings about the closing of the switching means on the conduit between the reservoir and the pumping means, and the delivery of an instantaneous dose of fluid into the outlet conduit.

Further, the rotation of the disks in the direction $S_2$ makes it possible to trigger the automatic mechanical means for the delivery of a continuous dose of fluid into the outlet conduit. The adjustment of the rate of flow of the continuous dose is obtained by rotation of the disks in one or the other direction, $S_1$ or $S_2$, between their extreme positions.

The automatic mechanical means for the delivery of a continuous dose are inactive when the manual mechanical means for the delivery of an instantaneous dose are active and, vice versa, the manual mechanical means for the delivery of an instantaneous dose are inactive when the automatic mechanical means for the delivery of a continuous dose are active.

The switching means are formed, on the one hand, by a device which controls the rate of flow, arranged around the conduit which connects the reservoir to the pumping means, and on the other hand by a non-return device arranged on the outlet conduit to prevent any return of fluid into the pumping means and/or into the reservoir.

Furthermore, the switching means comprise a device for the braking/blocking of the flow controller.

The elastic means in accordance with the invention are formed of a spring, for instance a coil spring, the outer end of which is mechanically associated with the internal magnetic means while its inner end is associated with mechanical gear transmission means which transmit the tensile force and the movement of relaxation of the spring, on the one hand, to the regulating means and, on the other hand, to the pumping means.

The device according to the invention also comprises counting means which make it possible for the user to know the number of revolutions imparted to the internal disks and therefore to know, on the one hand, the degree of tension of the elastic means and the degree of filling of the pumping means and, on the other hand, the quantity of fluids injected manually at the time or automatically continuously.

The counting means consist of at least one hammer cooperating with at least one disk having protrusions and/or at least one resonant blade cooperating with at least one protrusion of the piston shaft of the pumping means, as well as means for amplifying the sounds given off by the hammer(s) and/or blade(s).

According to the invention, the pumping means are formed of a syringe with piston sliding within a cylinder, to the outlet of which the outlet conduit and the conduit connecting with the reservoir are connected in parallel.

The following description, read in conjunction with the accompanying drawings, which are given by way of illustration and not of limitation, will make it possible to understand how the invention can be reduced to practice.

FIG. 1 is a diagrammatic sectional view through the fluid injection device of the invention.

Figure 2A:
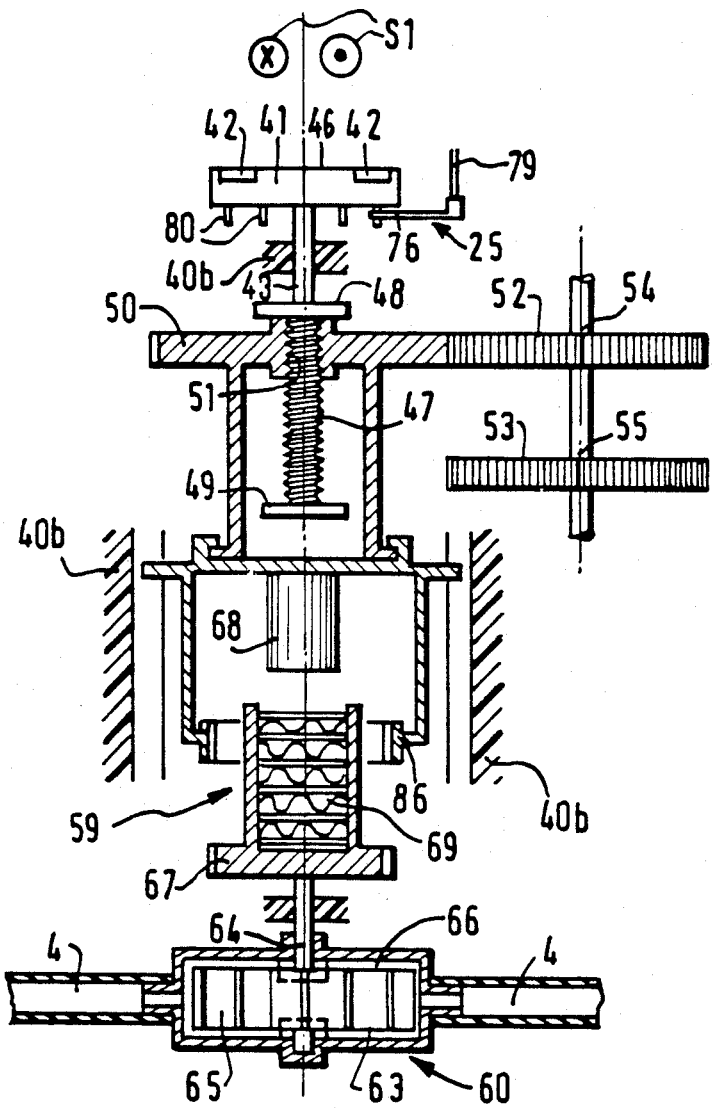
Figure 2B:
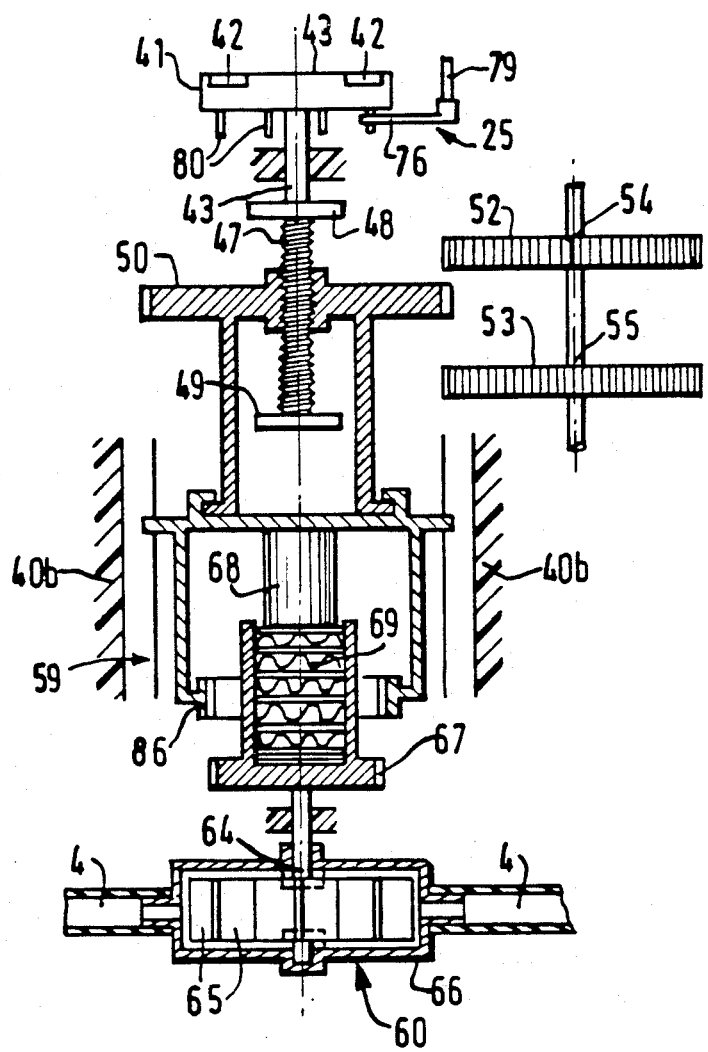
Figure 2C:
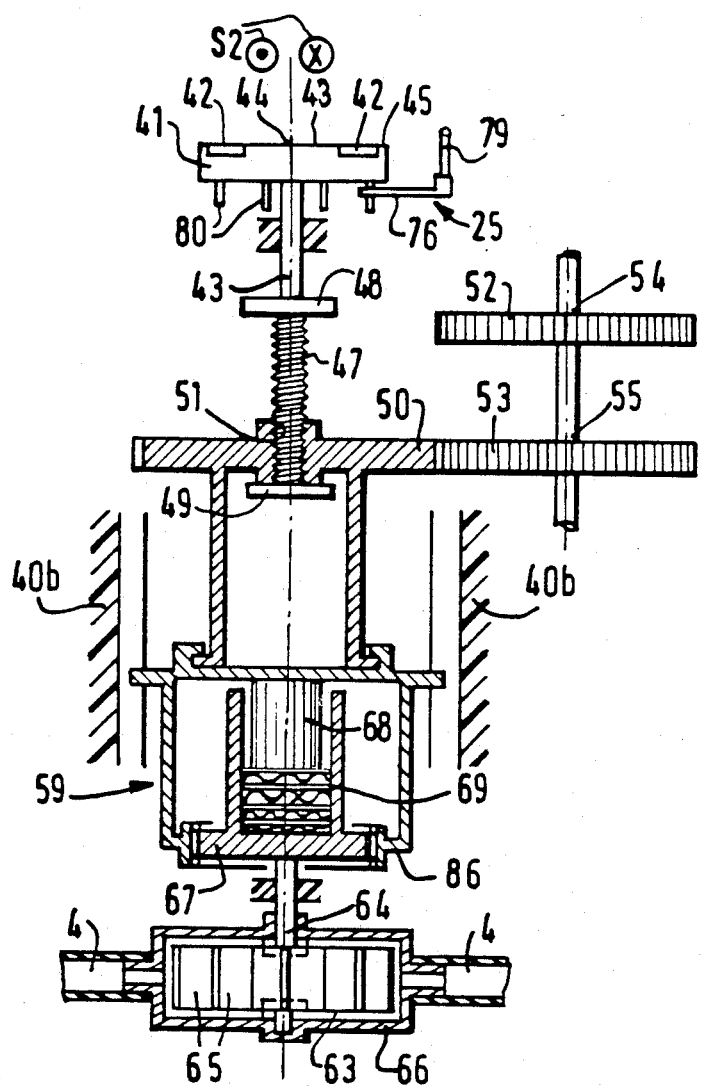

FIGS. 2a, 2b, 2c are diagrammatic views illustrating the kinematics of the internal magnetic drive means, the switching means, the mechanical transmission means and a part of the counting means. FIG. 2a corresponds to an extreme position of the internal magnetic disk in the direction $S_1$, FIG. 2b corresponds to an extreme position of the disk in the direction $S_2$, and FIG. 2c corresponds to an intermediate position.

The fluid injection device 1 shown in FIG. 1 is intended to be implanted in a patient suffering, for example, from diabetes. It has an implantable inner part and an external part.

The device 1 in accordance with the invention comprises a fluid outlet conduit 3, a fluid reservoir 5 connected by a conduit 4 to pumping means 8 which make it possible to remove fluid from the reservoir 5 and send it into the outlet conduit 3. Mechanical switching means 7 has the function of connecting or disconnecting conduits 3, 4.

The device 1 furthermore has mechanical elastic means 9, magnetic drive means 10 formed of an external part 10a and an implanted internal part 10b, as well as mechanical means 12 for regulating the relaxation of the elastic means 9.

The external part 10a and the internal part 10b of the magnetic drive means 10 can cooperate, by magnetic interaction, with each other through the skin 30 of the patient.

The external part 10a is formed of a disk 31 which bears one or more magnetized magnetic bars 32 defining a South pole and a North pole which are substantially symmetrical to each other with respect to the center 34 of the disk 31. A rotary shaft 33 is rigidly associated perpendicularly to the disk 31 at its center 34. Manual drive means 35 make it possible to drive the disk 31 in rotation around the shaft 33.

These manual drive means 35 are formed of an actuating member 36, for instance a crank 36 or the equivalent, associated with a gear train 37, the last driving pinion of which cooperates with a driven pinion 38 rigidly fastened to the shaft 33 of the disk 31. Thus, when the patient turns the actuating member 36 in a given direction, the external disk 31 also turns in a given direction. If the patient turns the actuating member 36 in the other direction, the disk 31 turns in said other direction. The step-down ratio of the gear train 37 is adapted to the size of the device and to the power of the magnetic interaction of the external part 10a with the internal part 10b in order to turn the disk 31 at a speed such that the corresponding disk 41 of the internal part 10b fully follows along in the movement of the disk 31 of the external part 10a.

The entire external part 10a is contained within a housing 40a of generally bell shape which supports the shaft 33, for instance via at least two bearings, and which surrounds the magnetic disk 31 and the manual drive means 35, the actuating member 36 extending through the outside of the housing 40a so as to be accessible.

The housing 40a is preferably open opposite the face 39 of magnetic cooperation of the disk 31 of the external part 10a with the disk 41 of the internal part 10b.

The internal part 10b of the magnetic means 10 is therefore formed of a disk 41 bearing one or more magnetic bars 42 which define a South pole and a North pole which are substantially symmetrical to each other with respect to the center 44 of the disk 41. A rotary shaft 43 is rigidly associated with the disk 41, perpendicular to it, at its center 44 and extends from the inner face 45 of the disk 41.

The outer face 46 of the disk 41 cooperates magnetically with the face 39 of the disk 31 of the outer part 10a via a magnetic field B so that the placing in rotation of the external disk 31 produces the placing in rotation of the internal disk 41 in the same direction and at the same speed.

The entire internal part 10a is contained within a housing 40b which is impervious to the physiological fluids and can be implanted.

The rotary shaft 43 associated with the internal disk 41 has a helicoidal threading 47 of large screw pitch which extends at its free end between two radial stops 48, 49. A moveable pinion 50 having an internal thread 51 which corresponds to the thread 47 and cooperates with said thread 47 is free to move between the two stops 48, 49. The two stops 48, 49 define the axial displacement of the pinion 50 along the shaft 43. The moveable pinion 50 has external peripheral teeth which can cooperate with the teeth of two fixed pinions 52, 53 with shafts 54, 55 which are so arranged that the moveable pinion 50 meshes with the first fixed pinion 52 when it is in the vicinity of the first radial stop 48 and with the second fixed pinion 53 when it is in the vicinity of the second radial stop 49.

The first fixed pinion 52, via a suitable set of gears, produces:

the tensioning of the elastic means 9, the displacement of a piston 56 in a cylinder 57 forming a syringe 58 of the pumping means 8, in order to fill the syringe 58.

The second fixed pinion 53, via a suitable set of gears, produces:

the displacement of a piston 56 in the cylinder 57 for the instantaneous ejection of a dose of product from the syringe 58 into the catheter 29.

When the moveable pinion 50 cooperates with one of the stops 48, 49, it becomes rigidly attached to the rotating shaft 43 and drives one of the fixed pinions 52, 53 respectively.

Furthermore, the moveable pinion 50, upon its axial displacement towards the second stop 49, drives a device 59 for the braking/blocking of a flow controller 60, arranged on the conduit 4 between the outlet 61 of the reservoir 5 and the outlet 62 of the pumping syringe 58.

The flow controller is formed for instance of a reel 60 comprising a rotor 63 which is integral with a rotary shaft 64 which can be braked or blocked by the braking/blocking device 59. The shaft 64 can turn freely in either direction of rotation. The rotor 63 has radial blades 65 which extend within a cylindrical circulation chamber 66 so that the rate of flow transmitted in the conduit 4 is proportional to the speed of rotation of the rotor 63 and of the blades 65 in the chamber 66.

When the moveable pinion 50 is in it upper position against the first stop 48 it meshes with the first fixed pinion 52, the braking/blocking device 59 is completely inactive and the rotor is free to rotate. The fluid can therefore flow freely in the conduit 4 from the reservoir 5 into the syringe 58, which is filled as a result of the suction created by the displacement of the piston 56 (FIG. 2a).

When the moveable pinion 50 is in its lower position against the second stop 49 and meshes with the second fixed pinion 53, the rotor 63 is completely blocked by the braking/blocking device 59. For this purpose, for instance, the translation of the moveable piston 50 towards the second stop 49 causes translation of a toothed ring 86 which is blocked in rotation with respect to the housing 40b and comes to cooperate with a pinion 67 integral with the shaft 64 of the rotor 63 so as to immobilize it (FIG. 2c).

In this case, the conduit 4 is closed by the blocked rotor 63 of the flow controller 60 and no fluid can flow from the reservoir 5 towards the syringe 58, or vice versa. Ejection of the fluid from the syringe 58 can therefore not take place in the direction towards the reservoir 5.

When the moveable pinion 50 is in an intermediate position between the two stops 48, 49 it is not meshed with either of the moveable pinions 52, 53. On the other hand, this intermediate position of the moveable pinion 50 induces a braking moment in the braking/blocking device 59, which moment brakes the rotation of the shaft 64 of the rotor 63 of the flow controller device 60.

The braking moment increases as the moveable pinion 50 approaches the second stop 49 from a value of zero when the moveable pinion 50 is against the first stop 48 to a blocking value when the moveable pinion is against the second stop 49. For example, the regulating of the braking is obtained by a pusher 68 which is locked in rotation with respect to the housing 40b and associated in axial translation with the moveable pinion 50, and compresses an elastic friction device 69 against a plate which is integral with the shaft 64 of the rotor 63. The elastic friction device 69 is formed, for instance, of a stack of friction disks separated by elastic members or, as a variant, by one or more cylinders of elastic material or the like. The closer the moveable pinion 50 is to the second stop 49 the more the pusher 68 compresses the friction device 69 and the greater the braking moment is.

In this intermediate position of the moveable pinion 50, the relaxation of the elastic means 9 results in the continuous automatic regular displacement of the piston 56 in the direction of ejection of fluid into the catheter 29 and into the conduit 4 towards the reservoir 5 with a total flow q which is the sum of the flow $q_1$ in the catheter 29 and $q_2$ in the conduit 4 towards the reservoir 5. The adjustment of the braking by the braking/blocking device 59 permits the regulation of the flow $q_2$ in the conduit 4, and therefore the regulation of the flow $q_1$ in the catheter 29 since $q_1 = q - q_2$, q being imposed by the pressure exerted on the piston 56, which is assumed constant. The flow $q_1$ is maximum when the flow controller device 60 of the conduit 4 is in blocked position. This flow $q_1$ max is imposed by the force of relaxation of the elastic means 9. One has: $q_1$ max$=q$.

Furthermore, a nonreturn device 70 is advisedly provided on the outlet conduit 3 towards the catheter 29 in order to prevent any return of fluid from the catheter 29 into the syringe 58 and/or into the reservoir 5. For example, a reel 70 can be provided, formed of a rotor 71 having radial blades 72 on a shaft 95, similar to the flow controller 60, the shaft 95 being a freewheel shaft which permits free rotation of the rotor in only one direction, within a circulation chamber 73, so that the circulation of the fluid can take place through the device 70 only in the direction of the ejection of the fluid from the syringe 58 towards the catheter 29.

The conduit 4, connecting the outlet 61 of the reservoir 5 to the outlet 62 of the syringe 58 via the flow controller device 60 and the conduit 3, connecting the outlet 62 of the syringe 58 to the catheter 29 via the non-return device 70, are connected directly in parallel to the outlet 62 of the syringe 58.

The internal housing 40b contains the magnetic means 10b, the elastic means 9, the regulating means 11, the pumping means 8 formed of the syringe 58 and the piston 56, the mechanical transmission means 12 between these means 8, 9, 10b, 11 as well as the switching means 7.

The reservoir 5 is preferably made of implantable flexible material and is located outside the housing 40b, for instance around this closed tight housing 40b. The housing 40b therefore has, on the one hand, an outlet 61 of the conduit 3 towards the reservoir 5 and, on the other hand, an outlet 74 for the connection of the catheter 29. The reservoir 5 is also implanted and comprises, for instance, a filling lid 75 which can be pierced by a syringe needle without losing its tightness. Such lids are known in the prior art and therefore are not explained in detail here.

As a variant, which is not shown in the drawing, a feed conduit to the reservoir 5 can be provided in order to connect this implanted reservoir 5 to the outside by means of a tip for connection to an external conduit. Cocks or a three-way valve or a central cock can be provided in order to open or close each feed or outlet line or conduit leading to the reservoir 5 or in order to open or close connecting lines which respectively directly connect these conduits two by two, and this to the outlet branching 62 of the syringe 58.

The elastic means 9 are formed by a coil spring 18. An end of the spring 18 is associated with a winding device with non-return pawl 19, which, in its turn, is mechanically associated by mechanical gear transmission means to the first fixed pinion 52 which is controlled by the magnetic means 10, as previously described. The other end of the spring 18 is associated with the mechanical gear transmission means 12 which transmit the tension force and the movement of relaxation of the spring, on the one hand, to the regulating means 11 and, on the other hand, to the piston 56 of the syringe 58, so as to establish the continuous, uniform displacement of the piston 56 in the cylinder 57 of the syringe 58 for the ejection of a continuous dose of fluid into the catheter 29. The transmission means 12 transform the rotation imposed by the spring 18 into translation of the piston 56, for example of means of an endless screw or rack. A freewheel is advantageously provided on the last pinion of the transmission means 12, which is associated with the spring 18 and not associated with the second fixed pinion 53, directly controlling the displacement of the piston 56.

Counting means 25 permit the user to know the number of revolutions imposed upon the internal disk 41 and therefore, on the one hand, the degree of tension of the elastic means 9 and the degree of filling of the syringe 58 and, on the other hand, the quantity of fluid manually ejected at the time or automatically injected continuously.

These counting means 25 are formed of at least one small hammer 76 which cooperates with the internal disk 41 rigidly connected to the shaft 43. The hammer 76 is pulled back against disk 41 by an elastic return means such as a coil spring (not shown) arranged around the pivot pin 79 of the hammer 76. The disk 41 is of resonant material and has protrusions 80 which are arranged uniformly on the edge of the disk 41 with which the hammer 76 cooperates. For example, the protrusions 80 are radial and the hammer 76 is substantially tangent to the disk 41. When the disk 41 turns, driven by the shaft 43, the protrusions 80 pass under the hammer 76, which causes the giving off of a brief sound. The shape of the protrusions can be so adapted that the sound emitted in one direction of rotation of the shaft 43 is different from the sound emitted in the other direction of rotation of the shaft 43. As a variant, one can provide two different hammers 76 and/or two different disks 41 in order to give off different sounds in each direction of rotation of the shaft 43.

Means 90 for the amplification of the sounds given off by the hammer (s) 76 can be provided, for instance a microphone 91 which is applied to the skin 30 on the outside, in the vicinity of the place where the internal magnetic part 10b is implanted. The microphone is connected to an amplifier which sends the amplified sound to a loudspeaker and/or transforms the acoustic signal into digital pulses which are counted in at least one register and displayed, for instance, on a liquid crystal display.

The mechanical gear transmission means are preferably of such a nature that when the syringe 58 is completely filled, the spring 18 is tensioned to the maximum, the relaxation of the spring making it possible to completely empty the syringe 58. A blocking means can advantageously be provided in order to prevent excessive winding of the spring 18. For example, the first fixed pinion 52 brings about the displacement of the piston 56 which, in its turn, brings about the winding of spring 18. Thus when the piston 56 arrives against the stop, the syringe 58 being full, the movement is blocked and the spring 18 is no longer wound.

Finally, either arrival of the piston 56 at the end of its stroke when the syringe 58 is full and/or empty may be detected by a projection 81 which is rigidly connected to the shaft of the piston and cooperates with one and/or two resonant blades 82, 83 when the piston 56 arrives at either end of its stroke. The blades 82, 83 then give off brief tones of frequencies different from the hammer(s) 76 and different from each other.

The invention operates in the following manner:

With the exception of the external part 76 housed in housing 40a (principally 10a of the magnetic drive means 10 and any electronic amplification means 90), the entire device 1 is implanted in the body of a patient. The implantation is effected in such a manner that the internal magnetic disk 41 is directly below the skin and can magnetically cooperate with the external disk 31.

The catheter 29 terminates in an injection device, for instance a needle, which penetrates into a vein, the peritoneum, or the like.

In order to actuate and drive the implanted device 1, the patient applies the external part 10a in the neighborhood of the internal part 10b of the magnetic drive means 10 and actuates the manual drive means 35 in one direction or the other, as required.

When the device 1 is implanted in the patient, the syringe 58 is empty and the piston 56 is at the end of its stroke against the outlet 62 of the cylinder 57. The internal disk 41 therefore cannot turn if it meshes with the second fixed pinion 53. The counting means 25 will therefore remain inactive if the patient attempts to turn in the wrong direction $S_2$. On the other hand, if the patient turns in the proper direction $S_1$, then the moveable pinion cooperates with the first fixed pinion 52, which brings about the winding of the spring 18, the placing in inactive condition of the braking/blocking device 59 and the filling of the syringe 58 with fluid coming from the reservoir 5 via the conduit 4. When the sound emitted by the blade 82 indicates that the syringe 58 is full and/or that the blocking means are active, the patient knows that the syringe 58 is full. He can then inject an instantaneous dose manually by turning in the opposite direction $S_2$. After a certain number of clicks, for example four, the moveable pinion 50 cooperates with the second fixed pinion 53, which brings about the manual administration of the fluid. By counting the number of clicks emitted by the counting means 25, the quantity administered manually is verified. When the instantaneous dose is sufficient, the patient again turns in the direction $S_1$, which causes the moveable pinion 50 to rise to an intermediate position corresponding to a given value of the flow of the continuous dose. The larger the number of clicks in the direction $S_1$, the less the braking/blocking means 59 brakes the flow controller device 69 on the conduit 4 and the greater the return flow towards the reservoir 5, and therefore the smaller the volume administered continuously.

Of course, the number of clicks emitted by the counting means 25 is standardized and coded. An electronic device of the amplifying means preferably decodes the information and posts the true values, namely volume injected manually and volume injected automatically. The sound emitted by the blade 83, which indicates that the syringe 58 is empty, advantageously triggers an acoustic and/or visual alarm signal.

What is claimed is:

1. A fluid injection device comprising:
   an implantable fluid reservoir;
   an implantable catheter for injecting fluid contained in said reservoir into a patient, said catheter being connected to said reservoir;
   an implantable pumping means for pumping fluid from said reservoir to said implantable catheter;
   an implantable elastic means for actuating said pumping means;
   an implantable mechanical flow regulating means for regulating said elastic means to cause said pumping means to deliver a continuous dose of fluid to said catheter;
   a magnetic drive means for selectively tensioning said elastic means and for selectively driving said pumping means to deliver an instantaneous dose of fluid to said catheter, said magnetic drive means including a first implantable part and a second non-implantable part cooperating with each other through the skin of the patient via a magnetic field;
   an implantable gear transmission means for transmitting the motion of said first implantable part of said drive means selectively to said pumping means and selectively to said elastic means, said transmission means being capable of tensioning said elastic means thereby rendering said elastic means active, said transmission means being further capable of cooperating with said pumping means to fill said pumping means with fluid from said reservoir and to selectively manually deliver an instantaneous dose of fluid to said catheter independently of said elastic means; and
   an implantable flow-adjustment means for continuous adjustment of the rate of fluid flow to said catheter from said pumping means, said first implantable part of said drive means cooperating with said flow adjustment means when said pumping means is activated by said elastic means and when said first implantable part does not cooperate with said elastic means or said pumping means.

2. A device according to claim 1, wherein said implantable gear transmission means comprises:
   a first pinion capable of being rotatably engaged with said first implantable part of said drive means;
   a set of gears, said gears when in cooperation with said first pinion, producing the tensioning of said elastic means and the filling of said pumping means; and
   a second pinion capable of being rotatably engaged with said first implantable part of said drive means, said second pinion, via said set of gears, causing said pumping means to deliver an instantaneous dose of fluid into said catheter, said internal implantable part of said drive means cooperating with only one of said first and second transmission pinions or with none of them.

3. A device according to claim 2, wherein said pumping means comprises a syringe including a first outlet conduit and a second conduit connecting said syringe to said reservoir wherein said first outlet conduit connecting said syringe to said catheter and said second conduit are connected in parallel to said outlet of said syringe, and wherein said flow adjustment means comprises a flow controller device which controls the back-flow of fluid from said syringe to said reservoir, said flow controller being arranged on said second conduit.

4. A device according to claim 3, including a non-return device arranged on said first outlet conduit, said non-return device preventing any return of fluid from said catheter into said pumping means or into said reservoir.

5. A device according to claim 3, wherein said flow controller closes said second conduit when said first implantable part of said drive means cooperates with said second pinion to allow manual delivery of an instantaneous dose of fluid.

6. A device according to claim 3, wherein said first implantable part of said drive means cooperates with said flow controller to let a non-zero back flow of fluid pass to said second conduit, the non-zero value of the back flow depending on the position of said first implantable part of said drive means when said first implantable part of said drive means does not cooperate with said first and second pinions and is in an intermediate position between the two extreme positions from which it cooperates with one of said first or second pinions.

7. A device according to claim 3, wherein said flow controller closes said second conduit when said internal implantable part of said magnetic drive means cooperates with said second pinion to allow manual delivery of an instantaneous dose of fluid.

8. A device according to claim 3, wherein said internal implantable part of said magnetic drive means cooperates with said flow controller to let a non-zero back flow of fluid pass to said second conduit, the non-zero value of the back flow depending on the position of said internal implantable part of said magnetic drive means when said internal implantable part of said magnetic drive means does not cooperate with said first and second pinions and is in an intermediate position between the two extreme positions from which it cooperates with one of said first and second pinions.

9. A device according to claim 2, wherein said elastic means comprises a coil spring, an end of which is connected via said set of gears, to said first pinion, while the other end of said spring cooperates with said gear transmission means which transmits the movement caused by the relaxation of said spring to said regulating means and said pumping means.

10. A device according to claim 2, wherein said first implantable part and said second non-implantable part magnetically cooperate with each other through the skin of a patient such that the rotation of said non-implantable part induces the rotation of said first implantable part in the same direction at at least substantially the same speed, said first implantable part being rotatably mounted on a rotary shaft which is mounted in an implantable housing containing all said implantable means and said first implantable part of said drive means, said rotary shaft having a helicoidol thread which extends between a first and second radial stop, the device further comprising a moveable pinion having an internal thread cooperating with said helicoidol thread of said rotary shaft of said implantable part, so that said moveable pinion can be moved in an axial translatory motion between said two stops, said moveable pinion being rotatably attached to said rotary shaft and meshing with said first pinion when said moveable pinion is in the vicinity of said first radial stop, said moveable pinion being rotatably attached to said rotary shaft and meshing with said second pinion when said moveable pinion is in the vicinity of said second radial stop, said moveable pinion meshing with neither said first pinion nor said second pinion when said moveable pinion is in an intermediate position between said first and second radial stops, said moveable pinion cooperating with said flow adjustment means in its axial translatory motion in order to vary the rate of flow of fluid according to the position of said moveable pinion between said two radial stops so that the rotation of said drive parts in a first direction S1 from and beyond an extreme position produces the meshing and the rotation of said moveable pinion with said first pinion, and thus the tensioning of said elastic means and the filling of said pumping means and the rotation of said drive parts in a second direction S2 from and beyond another extreme position produces the meshing and the rotation of said moveable pinion with said second pinion, and thus the delivery of an instantaneous dose of fluid, and the rotation of said magnetic drive disks in either direction S1 or S2 between said two extreme positions produces the meshing of said moveable pinion with neither of said first and second pinions, and thus the automatic delivery of a continuous dose of fluid into said outlet conduit under the action of said pumping means activated by said elastic means, and the adjustment of the rate of flow of fluid delivered.

11. A device according to claim 10 wherein said flow adjustment means comprises a flow controller device comprising
a reel, said reel comprising:
a rotary shaft;
a rotor mounted on said rotary shaft;
radial blades integral with said rotary shaft, said radial blades extending outwardly from said rotary shaft;
a cylindrical circulation chamber, said radial blades extending within said chamber such that the rate of fluid flow transmitted to said outlet conduit is proportional to the speed of said rotor and of said blades in said chamber;
a pusher locked in rotation with respect to said housing, and cooperating with said movable pinion in said axial translatory motion; and
a breaking/blocking device of said rotor wherein said pusher acts upon said breaking/blocking device in a progressive manner according to the position of said moveable pinion between said radial stops in order to vary the rate of flow of fluid passing through said flow controller.

12. A device according to claim 10, further comprising counting means for denoting the number of turns imposed upon said first implanted part, said counting means including means for indicating the degree of tension of said elastic means and the degree of filling of said pumping means when said first implantable part is rotated in a first direction, said counting means further including means for indicating the amount of fluid manually instantaneously injected when said first implantable part is rotated in a second direction, and said counting means including means for indicating the rate of flow of fluid automatically continuously ejected when said first implantable part is selectively rotated in said first and second directions.

13. A device according to claim 12, wherein said counting means comprises sound means giving off regular sounds according to the rotation of said first implantable part of said drive means.

14. A device according to claim 13, further comprising means for amplification of sounds given off by said sound means.

15. A device according to claim 1, wherein said first implantable part and said second non-implantable part magnetically cooperate with each other through the skin of a patient such that the rotation of said second non-implantable part induces the rotation of said first implantable part in the same direction at at least substantially the same speed.

* * * * *